US010478265B2

(12) United States Patent
DeFusco et al.

(10) Patent No.: US 10,478,265 B2
(45) Date of Patent: Nov. 19, 2019

(54) CRANIAL FIXATION DEVICE

(71) Applicant: Integra LifeSciences Corporation, Plainsboro, NJ (US)

(72) Inventors: Michael A. DeFusco, North Attleboro, MA (US); Gregory M. Schorn, Milford, MA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 266 days.

(21) Appl. No.: 15/476,088

(22) Filed: Mar. 31, 2017

(65) Prior Publication Data

US 2018/0280106 A1    Oct. 4, 2018

(51) Int. Cl.
| | | |
|---|---|---|
| *A61B 90/14* | (2016.01) | |
| *A61M 25/02* | (2006.01) | |
| *A61B 17/34* | (2006.01) | |
| *A61B 90/10* | (2016.01) | |

(52) U.S. Cl.
CPC ............ *A61B 90/14* (2016.02); *A61M 25/02* (2013.01); *A61B 2017/347* (2013.01); *A61B 2017/349* (2013.01); *A61B 2090/103* (2016.02); *A61M 2025/024* (2013.01); *A61M 2025/028* (2013.01); *A61M 2025/0286* (2013.01); *A61M 2210/0687* (2013.01)

(58) Field of Classification Search
CPC ............ A61B 90/14; A61B 2017/349; A61B 2017/347; A61B 2017/00477; A61B 17/3423; A61B 2090/103; A61B 90/11; A61M 2025/0286; A61M 2210/0687; A61M 25/02; A61M 2025/024; A61M 2025/0246; A61M 2025/028; A61M 39/0247; A61M 2039/025; A61N 1/0539

USPC ......... 604/174, 175; 606/129, 130; 607/115, 607/116; 128/897–899
See application file for complete search history.

(56) References Cited

U.S. PATENT DOCUMENTS

| | | |
|---|---|---|
| 4,335,908 A | 6/1982 | Burge |
| 4,809,694 A | 3/1989 | Ferrara |
| 4,903,707 A | 2/1990 | Knute et al. |
| 5,222,747 A | 6/1993 | McGarvey |
| 5,332,234 A | 7/1994 | Forch et al. |
| 5,405,388 A | 4/1995 | Fox |
| 5,455,391 A | 10/1995 | Demesmaeker et al. |
| 5,891,100 A | 4/1999 | Fleckenstein |
| 5,954,687 A | 9/1999 | Baudino |
| 6,080,134 A | 6/2000 | Lotti et al. |
| 6,152,933 A | 11/2000 | Werp et al. |

(Continued)

FOREIGN PATENT DOCUMENTS

WO    97/42870    11/1997

OTHER PUBLICATIONS

Integra LifeSciences Corporation, "Integra Licox Brain Tissue Oxygen Monitoring: Directions for Use REF IP2.P*, Complete Brain Probe Kit", 2013 (see attached) (Year: 2013).*

(Continued)

*Primary Examiner* — Navin Natnithithadha
*Assistant Examiner* — Sunita Reddy
(74) *Attorney, Agent, or Firm* — Troutman Sanders LLP (57) ABSTRACT

Cranial fixation devices are provided. For example, a cranial fixation device may include positive stops that provide visual and tactical feedback when a predetermined compression is applied once a medical device is inserted therein and placed in position.

18 Claims, 9 Drawing Sheets

(56) References Cited

U.S. PATENT DOCUMENTS

| | | | |
|---|---|---|---|
| 6,454,774 B1 | 9/2002 | Fleckenstein | |
| 6,618,623 B1* | 9/2003 | Pless | A61N 1/375 |
| | | | 607/116 |
| 6,623,490 B1 | 9/2003 | Crane et al. | |
| 6,673,022 B1 | 1/2004 | Bobo et al. | |
| 6,752,812 B1* | 6/2004 | Truwit | A61B 90/11 |
| | | | 606/1 |
| 7,604,658 B2 | 10/2009 | Wilson et al. | |
| 7,780,679 B2 | 8/2010 | Bobo, Sr. et al. | |
| 8,308,781 B2 | 11/2012 | Wilson et al. | |
| 2001/0003156 A1* | 6/2001 | Gill | A61B 90/11 |
| | | | 606/130 |
| 2001/0027271 A1* | 10/2001 | Franck | A61B 90/11 |
| | | | 600/426 |
| 2002/0052610 A1* | 5/2002 | Skakoon | A61B 34/20 |
| | | | 606/129 |
| 2002/0169382 A1 | 11/2002 | Bobo, Sr. | |
| 2003/0209863 A1 | 11/2003 | Gregoire | |
| 2004/0034367 A1* | 2/2004 | Malinowski | A61B 90/11 |
| | | | 606/129 |
| 2004/0102828 A1* | 5/2004 | Lowry | A61N 1/0531 |
| | | | 607/116 |
| 2004/0243145 A1* | 12/2004 | Bobo, Sr. | A61B 5/031 |
| | | | 606/129 |
| 2004/0267284 A1* | 12/2004 | Parmer | A61B 90/11 |
| | | | 606/130 |
| 2005/0143799 A1* | 6/2005 | Black | A61B 5/6864 |
| | | | 607/116 |
| 2005/0182420 A1* | 8/2005 | Schulte | A61N 1/0539 |
| | | | 606/130 |
| 2006/0173522 A1* | 8/2006 | Osorio | A61B 5/6864 |
| | | | 607/116 |
| 2007/0233158 A1* | 10/2007 | Rodriguez | A61N 1/0531 |
| | | | 606/130 |
| 2008/0172068 A1* | 7/2008 | Adams | A61B 5/6864 |
| | | | 606/130 |
| 2009/0076456 A1* | 3/2009 | Armstrong | A61B 17/3462 |
| | | | 604/167.06 |
| 2009/0112084 A1* | 4/2009 | Piferi | G01R 33/286 |
| | | | 600/421 |
| 2009/0118610 A1* | 5/2009 | Karmarkar | A61B 5/0476 |
| | | | 600/420 |
| 2009/0253977 A1* | 10/2009 | Kipke | A61B 5/04001 |
| | | | 600/378 |
| 2010/0023020 A1* | 1/2010 | Barker | A61B 90/57 |
| | | | 606/129 |
| 2010/0312193 A1 | 12/2010 | Stratton et al. | |
| 2011/0144440 A1* | 6/2011 | Cropper | A61B 17/3421 |
| | | | 600/203 |
| 2012/0245529 A1 | 9/2012 | Hummen et al. | |
| 2013/0066410 A1* | 3/2013 | Funderburk | A61F 2/2875 |
| | | | 607/116 |
| 2013/0304216 A1 | 11/2013 | Paspa et al. | |
| 2014/0276529 A1* | 9/2014 | Bodner | A61M 25/02 |
| | | | 604/500 |
| 2015/0141926 A1* | 5/2015 | Asaad | A61M 25/02 |
| | | | 604/175 |
| 2015/0182728 A1 | 7/2015 | Khalaj et al. | |

OTHER PUBLICATIONS

Written Opinion for PCT/US2018/025691 dated Jun. 6, 2018, 9 pages.

Integra Life Sciences, "Integra Licox Brain Tissue Oxygen Monitoring IP2P Complete Brain Probe Kit", 0454888-2-EN, 2 pages (2016).

* cited by examiner

CRANIAL FIXATION DEVICE

FIELD OF THE DISCLOSURE

This disclosure relates to cranial fixation devices or bolts for securing medical devices to the head and methods of operation thereof.

BACKGROUND

Cranial fixation devices are used to secure medical devices to the head and control the depth of the medical devices inserted into the brain within the skull. The medical devices can include a catheter or probe. The catheter or probe is introduced into a lumen or hole of the fixation device and into a corresponding hole in the skull.

The catheter or probe is secured to the skull by threading the cranial fixation device into the cranium and crimping the catheter or probe cable with compression. However, the inventors noticed that currently available compression type fittings and fixation devices used to crimp the catheter or probe cable do not have a positive stop or any visual means of knowing when the cable of a medical device is properly clamped. This results in either over or under compression. When the compression fitting or fixation device is not tightened enough, the cable can slip, however, when over compressed or tighten, signal interference may occur.

For example, when a fiber optic cable is used, over compression may cause interference or breaks in the optical signal.

Some cranial fixation devices use Luer-type fitting connections. However, when using a Luer-type fitting connection, the catheter or probe depth cannot be adjusted.

SUMMARY

Accordingly, disclosed is a cranial fixation device comprising a cap, a base and a compression grommet. The cap comprises a central body having a mating connector with a threaded portion projecting from a distal end of the central body, a pair of wings extending radially out from the central body and a first opening extending from a proximal end of the central body to the distal end of the central body and through the threaded portion of the mating connector. The base comprises a threaded central opening corresponding to the threaded portion of the mating connector, a distal threaded portion configured to engage with an opening in a skull, a pair of wings extending radially out from the threaded central opening and a second opening extending through the threaded central opening and the distal threaded portion. The threaded central opening is positioned on a proximal end of the base. The compression grommet is configured to be placed into the threaded central opening of the base. The compression grommet has a third opening extending from the proximal end to the distal end of the compression grommet. The openings, e.g., the first opening, the second opening and the third opening, are aligned when the cap mates with the base and forms an instrument lumen configured to accept a portion of an instrument cable. The threaded portion of the cap is configured to mate with the threaded central opening of the base. At least one of the wings of the pair of wings of the cap has a projection protruding in a direction towards the base. Additionally, each wing of the pair of wings of the base has a seat. When the instrument cable extends through the instrument lumen, the projection from at least one wing of the pair of wings of the cap and at least one of the seats in the pair of wings of the base are configured to create a torque stop when a predetermined compression of the compression grommet is applied by tightening the cap on the base. When the predetermined compression of the compression grommet is applied, the compression grommet compresses against the instrument cable fixing the instrument cable in place at a determined depth.

Also disclosed is a cranial fixation device comprising a base. The base comprises a threaded central opening, a distal threaded portion, an opening and a pair of wings. The threaded central opening is positioned on a proximal end of the base and configured to mate with a mating connector of a cap. The distal threaded portion is configured to engage with an opening in a skull. The opening extending through the threaded central opening and the distal threaded portion. The opening is configured to receive a portion of an instrument cable. The pair of wings extend radially out from the threaded central opening. Each wing has a notch configured to receive another portion of the instrument cable.

Also disclosed is a cranial fixation device comprising a cap, a base and a compression grommet. The cap comprises a central body having a mating connector with a threaded portion projecting from a distal end of the central body and a first opening extending from a proximal end of the central body to the distal end of the central body and through the threaded portion of the mating connector. The base comprises a threaded central opening corresponding to the threaded portion of the mating connector, a distal threaded portion configured to engage with an opening in a skull, a pair of wings extending radially out from the threaded central opening and a second opening extending through the threaded central opening and the distal threaded portion. The threaded central opening is positioned on a proximal end of the base. The compression grommet is configured to be placed into the threaded central opening of the base. The compression grommet has a third opening extending from the proximal end to the distal end of the compression grommet. Each opening, e.g., the first opening, the second opening and the third opening, is aligned when the cap mates with the base and forms an instrument lumen configured to accept a portion of an instrument cable. The threaded portion of the cap is configured to mate with the threaded central opening of the base. When the instrument cable extends through the instrument lumen, the dimensions of the threaded central opening and the threaded portion are configured to create a torque stop when a predetermined compression of the compression grommet is applied by tightening the cap on the base. When the predetermined compression of the compression grommet is applied, the compression grommet compresses against the instrument cable fixing the instrument cable in place at a determined depth.

BRIEF DESCRIPTION OF THE DRAWINGS

The drawings are provided for illustrative purpose only and do not necessarily represent practical examples of the present disclosure to scale. In the figures, the same reference signs are used to denote the same or like parts.

DETAILED DESCRIPTION

Figure 1:
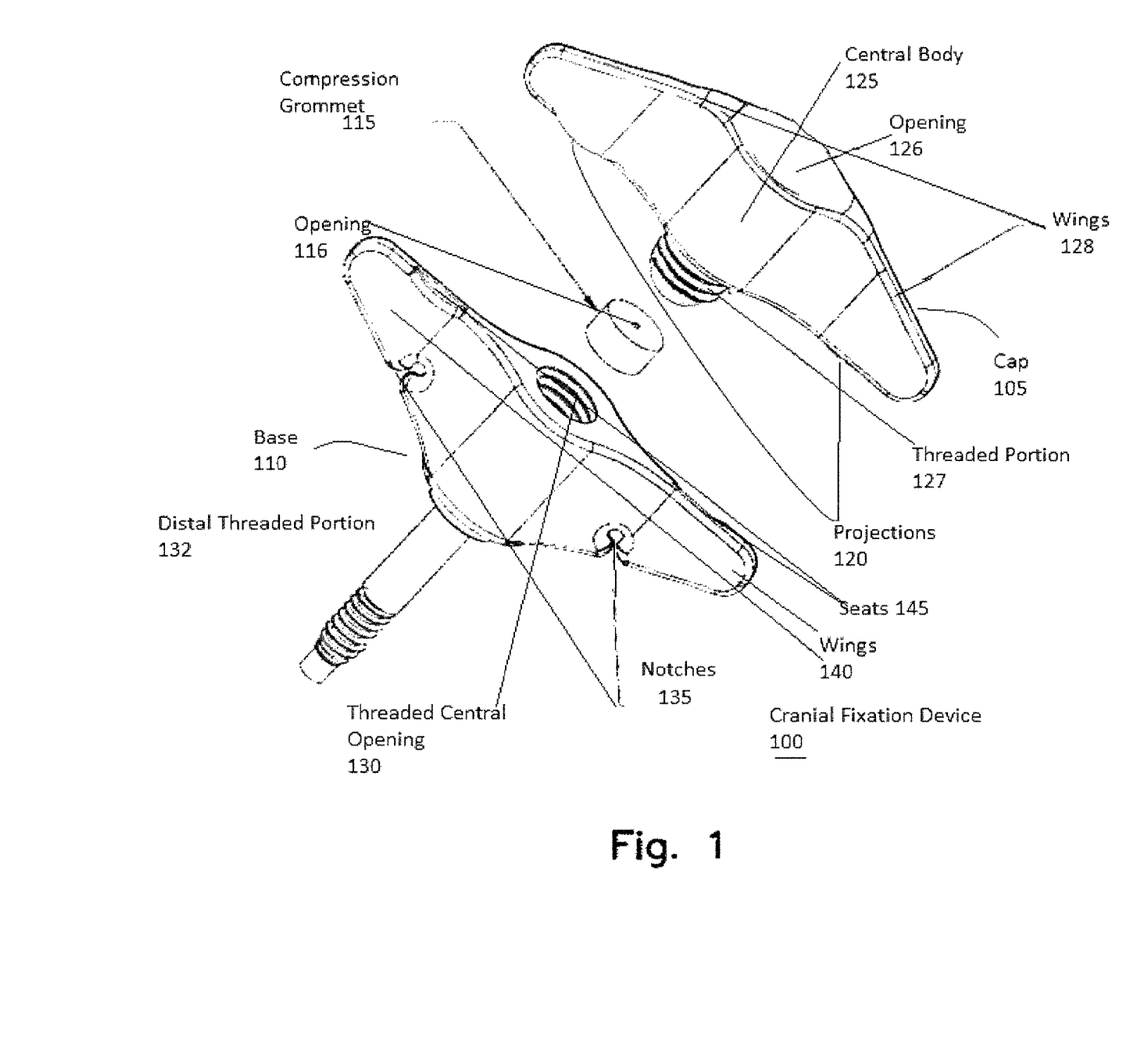
FIG. 1 is an exploded view of a cranial fixation device in accordance with aspects of the disclosure.

As shown in FIG. 1, the cranial fixation device 100 comprises a cap 105, a base 110 and a compression grommet 115. The base 110 has a hollow distal threaded portion 132 for securing the cranial fixation device 100 into a hole in a skull. The hole is preformed. The distal threaded portion 132 is hollow having an opening that is dimensioned to allow a portion of the cable of the medical device to be inserted there through. The base 110 also has a body having a threaded central opening 130. The threaded central opening 130 has a female threading. The female threading is for mating with a male threading in the cap 105. The threaded central opening 130 is dimensioned to allow the cable of the medical device to be inserted there through. The opening of the distal threaded portion 132 and the opening of the threaded central opening are aligned.

The compression grommet 115 is dimensioned to be insertable into the opening of the threaded central opening 130. The compression grommet 115 has an opening going through from the proximal to the distal end thereof. When inserted into the threaded central opening 130, the opening of the compression grommet 115 is also aligned with opening of the distal threaded portion 132 and the opening of the threaded central opening. The compression grommet 115 can be made from silicone.

The body of the base 110 has wings 140 extending outward to facilitate securing the base into the hole of the skull. In an aspect of the disclosure, each wing 140 including notches 135. As depicted, the notches 135 are located on the distal side of each wing 140. The notches 135 are configured and dimensioned to respectively receive a portion of a cable of medical device. Each notch 135 has a slot or opening that allows for the cable to be inserted. Once inserted, the cable is loosely secured within the notch 135. The notches 135 provide a strain relief for the cable. As depicted in FIG. 1, the notches are located symmetrically on the wings 140 with respect to the center of the fixation device, however, the location of the notches are not required to be symmetric.

Figure 4:
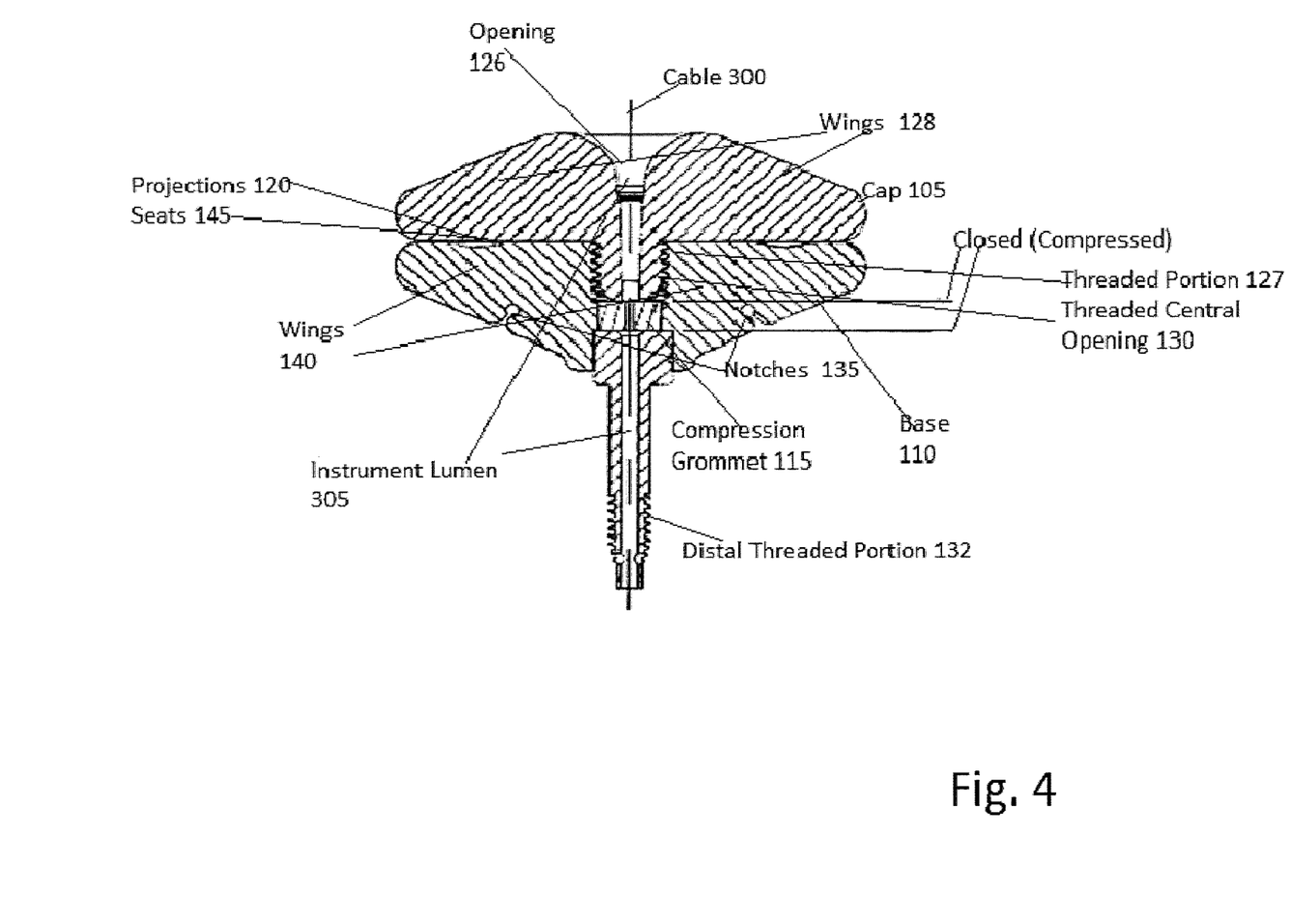

The cap 105 also has wings 128 extending outward to facilitate securing the cap to the base. As shown in FIG. 4 (closed position), the size of the wings 128 in the longitudinal direction of the cap is the same size as the wings 140 of the base in the longitudinal direction.

The cap 105 has a central body 125. The central body 125 has a generally cylindrical shape. The wings 128 extend outward from the central body 125. The central body 125 has an opening 126 extending therethrough. The opening extends from the proximal end to the distal end.

As seen in the sectional views of a cranial fixation device (FIGS. 3 and 4), the opening 126 is tapered. In other words, the opening 126 is larger on the proximal end than on the distal end. Advantageously, the tapered opening provides a benefit of preventing the cable of a medical device when it is inserted into the opening from bending at a right angle. For example, if the opening was not tapered, but rather straight, when a cable is inserted into the opening, the cable could be bent at a steep angle, which could result in the cable severing or having signal interference.

The cap 105 also includes a threaded portion 127 (mating connector with threading). The threaded portion 127 extends or projects distally from the central body 125. As shown in FIG. 1, the threaded portion 127 is a male threaded portion. When the cap 105 is placed on the base 110 and screwed on to secure the same to the base, the threaded portion 127 mates with the female threading of the threaded central opening 130 as will be described in detail later.

The threaded portion 127 also has an opening. The opening of the threaded portion 127 and the opening 126 of the central body 125 are aligned such that a cable of a medical device can be inserted therethrough.

At least one of the wings 128 of the cap 105 has a distal projection 120. Each wing 140 of the base 110 has a corresponding indentation or seat 145. As shown in FIG. 1, the cranial fixation device 100 has two projections 120, one on each wing 128 of the cap and two respective seats 145, one on each wing 140 of the base. However, two projections 120 on the cap 105 are not required. In an aspect of the disclosure, the cap 105 can have one distal projection 120 on a wing 128.

The dimensions of the at least one projection on the wings 128 matches the dimensions of the seats 145 on the wings 140 of the base. The combination of the at least one projection 120 and seats 145 of the wings of the base form a positive stop for the compression. Since the dimensions of the at least one projection and seats match, when mated, the distal end of the wings of the cap 105 and the proximal ends of the wings of the base 110 can be flush against each other when fully compressed and locked, e.g., closed position (see FIG. 4). This provides both a visual and tactile indication when desired compression is applied.

As described above, when the cap 105 is screwed on the base 110, the threaded portion 127 (of the cap) mates with the threaded central opening 130 (of the base 110). In an aspect of the disclosure, the length of the threading in both the threaded portion 127 and the threaded central opening 130 is set such that a predetermined compression can be applied to the medical device. In other words, the length of the respective threading is set such that when mated, the distal end of the wings of the cap and the proximal ends of the wings of the base can be flush against each other when fully compressed and locked, e.g., closed position, when a predetermined compression is applied (see FIG. 4). Moreover, when the predetermined compression is applied, the respective wings (of the cap and base are aligned). This also gives a visual indication when the desired (predetermined) compression has been applied.

Accordingly, in an aspect of the disclosure, the combination of the at least one projection and corresponding seats 145 and the length of the threading provides a positive stop with tactical and visual indications when a predetermined compression is applied. Thus, the disclosed cranial fixation device 100 allows for a repeatable compression of a medical device (cable thereof) without the problem of over or under tightening.

Figure 2:
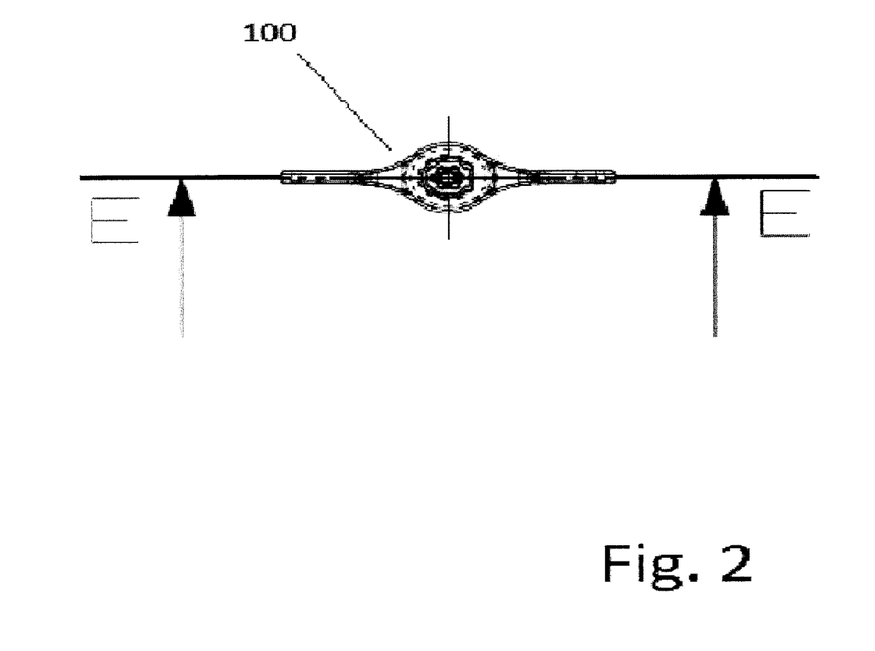
FIG. 2 is a top view of the cranial fixation device in accordance with aspects of the disclosure.
Figure 3:
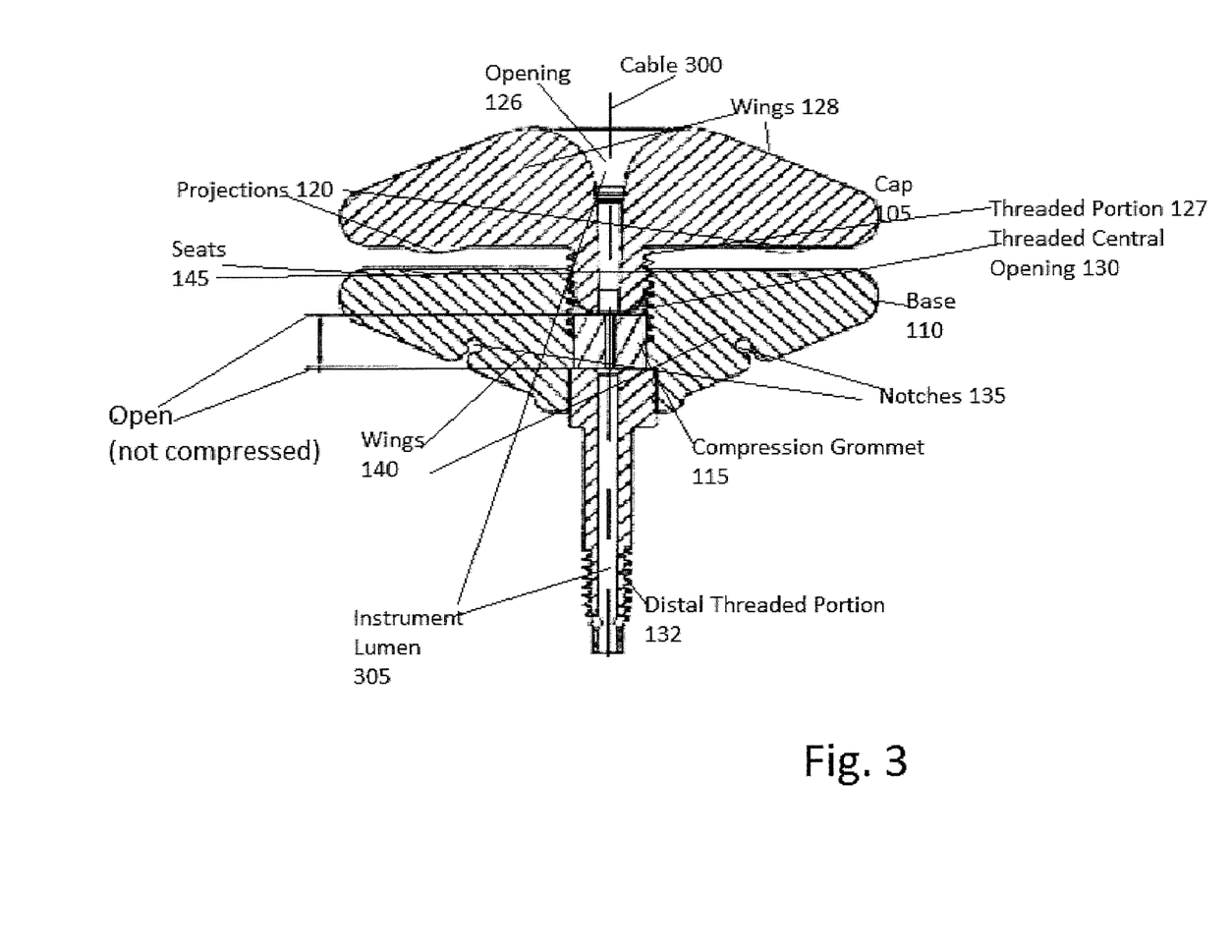
FIGS. 3-4 are sectional views of the cranial fixation device along the E-E line of FIG. 2.

FIGS. 3-4 are sectional views of the cranial fixation device 100 along the E-E line of FIG. 2.

FIG. 3 depicts a sectional view of the cranial fixation device 100 in an opened state, e.g., not compressed. FIG. 4 depicts a sectional view of the cranial fixation device 100 in a closed state, e.g., compressed. In both figures, the medical device cable 300 is depicted as a dashed line traversing the instrument lumen 305. In the opened state, not compressed, the cap 105 is positioned to contact the compression grommet 115. The threaded portion 127 of the cap 105 is partially mated with the threaded central opening 130. In order to close the cranial fixation device 100, the operator or user, twists or turns the wings 128 of the cap 105 to compress the compression grommet 115. Closing will occur once the medical device is position at a desired location with the skull, e.g., desired depth. By twisting the wings 128 of the cap 105, the threaded portion 127 of the cap further mates with the threaded central opening 130 of the base. The wings 128 of the cap 105 are twisted or turned until the projections 120 of the cap 120 engage with the seats 145 of the base 110. In an aspect of the disclosure, at the same time, the threaded portion 127 of the cap will be fully mated with the threaded central opening 130 of the base as shown in FIG. 4. FIG. 4 also shows the projections 120 of the cap engaged with the seats 145 of the base 110.

Thus, as shown in FIG. 4, the cable 300 is secured in position.

Figure 5:
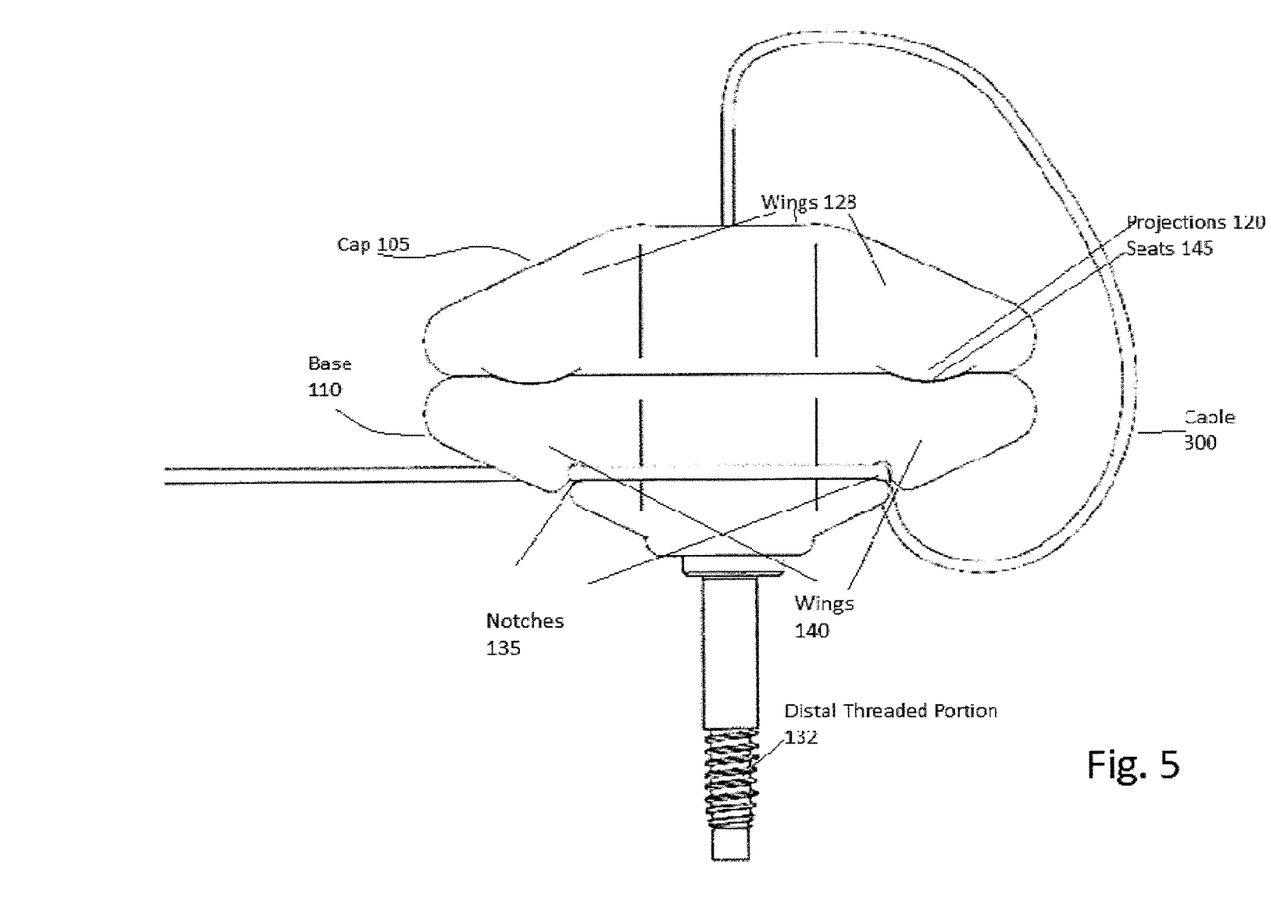
FIG. 5 is a view of the cranial fixation device with the cable of a medical device inserted in the lumen and notches in accordance with aspects of the disclosure.

FIG. 5 also depicts the cranial fixation device 100 in a closed position, e.g. compressed. FIG. 5 also shows the cable 300 inserted into the respective notches 135 of wings of the base 100. The cable 300 is also shown as being inserted into the lumen 305. The cable 300 extends between the respective notches 135 which provide strain relief.

While the cranial fixation device 100 is shown with both projections 120, seats 145 and notches 135, in another aspect of the disclosure, the notches can be removed.

A method for inserting a catheter or probe will now be described. The base 110 of the cranial fixation device 100 is inserted in a preformed opening in the skull. In particular, the user will twist the base 110 such that the distal threaded portion 132 engages in the opening. At the time the base 110 is inserted into the preformed opening, the compression grommet 115 may already be positioned within the threaded central opening 130. Alternatively, the compression grommet 115 can be inserted into the threaded central opening of the base 100 after the base 110 is inserted into the preformed opening. The cap 105 is aligned with the compression grommet 115 and base 110 in an opened state (uncompressed). Subsequently, the cable 300 of the catheter or probe is inserted into the instrument lumen and notches 135. Initially, the cable 300 is inserted in the opening 126 of the cap 105 and opening of the threaded portion 127. The cable 300 is then advanced into the opening 116 of the compression grommet 115. The cable 300 is further advanced into the distal thread portion 132 which has an opening. The cable 300 is subsequently advanced until, the catheter or probe is at a desired depth. When the catheter or probe is at a desired depth, the cranial fixation device 100 is closed, as described above. For example, the wings 128 of the cap 105 are twisted by the user causing the threaded portion 127 of the cap to further mate with the threaded central opening 130 of the base. The wings 128 of the cap 105 are twisted or turned until the projections 120 of the cap 120 engage with the seats 145 of the base 110. In an aspect of the disclosure, at the same time, the threaded portion 127 of the cap will be fully mated with the threaded central opening 130 of the base as shown in FIG. 4.

Additionally, when the catheter or probe is at a desired depth, the cable 300 is inserted into the notches 135.

Alternatively, instead of inserting the cable 300 of the catheter or probe into the cap 105, when the cap is aligned, the cable 300 of the catheter or probe can be inserted into the cap 105 prior to alignment.

Figure 6:
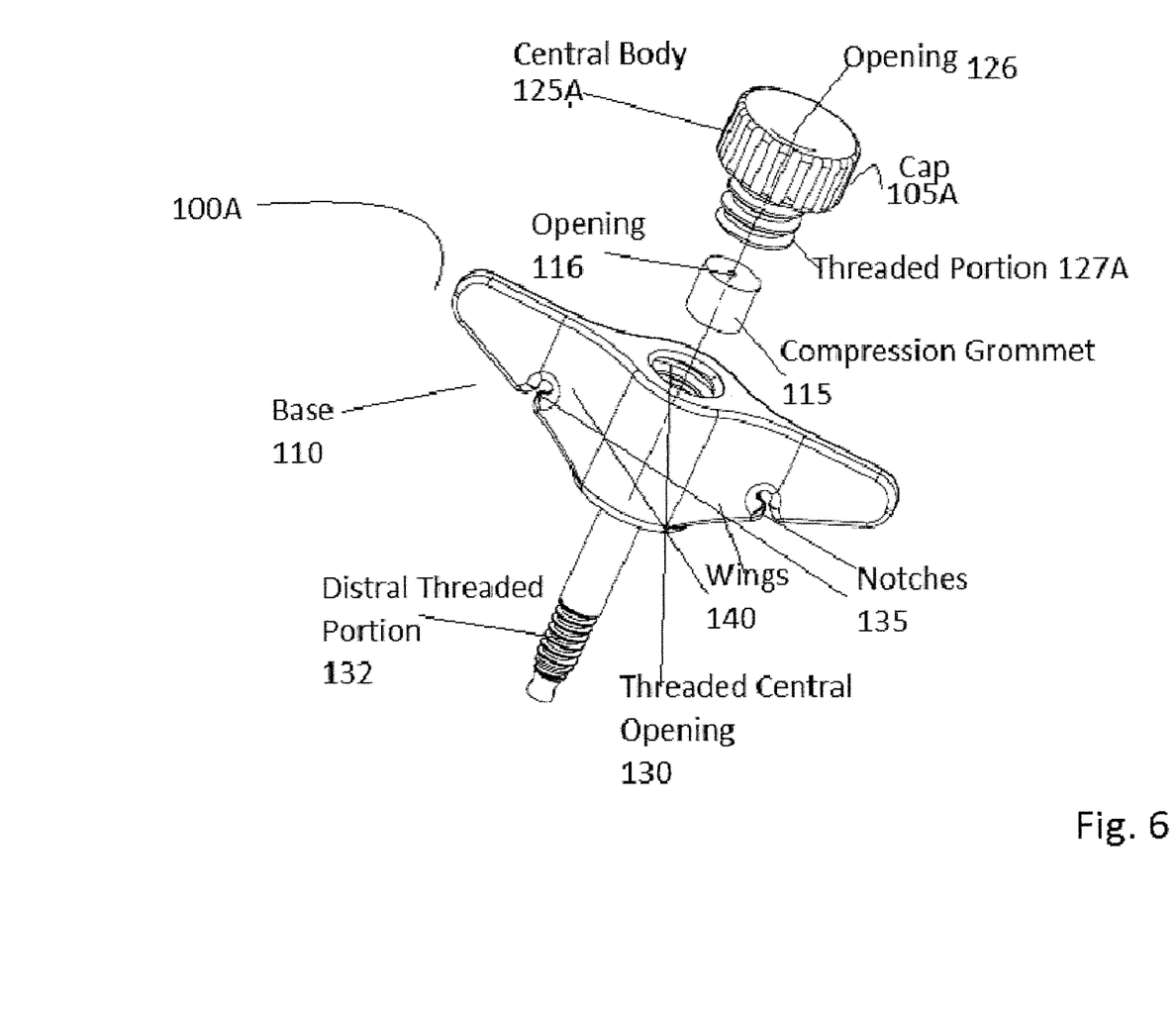
FIG. 6 is an exploded view of another cranial fixation device in accordance with aspects of the disclosure.

FIG. 6 is an exploded view of a cranial fixation device 100A in accordance with other aspects of the disclosure. The base 110 of the cranial fixation device 100A is the same as described above and therefore, will not be described again in detail. Additionally, the same reference numbers are used.

The cap 105A of the cranial fixation device 100A is different from the cap 105 of the cranial fixation device 100 in that the cap 105A does not include the wings. The cap 105 includes a central body 125A. The central body 125A has a cylindrical shape. The central body 125A has an opening 126. The opening 126 is similar to the opening in the cranial fixation device 100 and will not be described again in detail.

The cap 105A also includes a threaded portion 127A. The threaded portion 127A extends or projects distally from the central body 125A. As shown in FIG. 1, the threaded portion 127A is a male threaded portion. When the cap 105A is placed on the base 110 and screwed on to secure the same to the base, the threaded portion 127A mates with the female threading of the threaded central opening 130.

The threaded portion 127A also has an opening. The opening of the threaded portion 127A and the opening 126 of the central body 125A are aligned such that a cable of a medical device can be inserted therethrough.

When the cap 105A is screwed on the base 110, the threaded portion 127A (of the cap) mates with the threaded central opening 130 (of the base 110). In an aspect of the disclosure, the length of the threading in both the threaded portion 127A and the threaded central opening 130 is set such that a predetermined compression can be applied to the medical device. In other words, the length of the respective threading is set such that the distal end of the central body 125A is flush against the proximal end of the base when fully compressed and locked, e.g., closed position when a predetermined compression is applied (see FIG. 9). This also gives a visual indication when the desired (predetermined) compression has been applied.

Accordingly, in an aspect of the disclosure, the length of the threading provides a positive stop with tactical and visual indications of applying a predetermined compression. Thus, the disclosed cranial fixation device 100A allows for a repeatable compression of a medical device (cable thereof) without the problem of over or under tightening.

Figure 7:
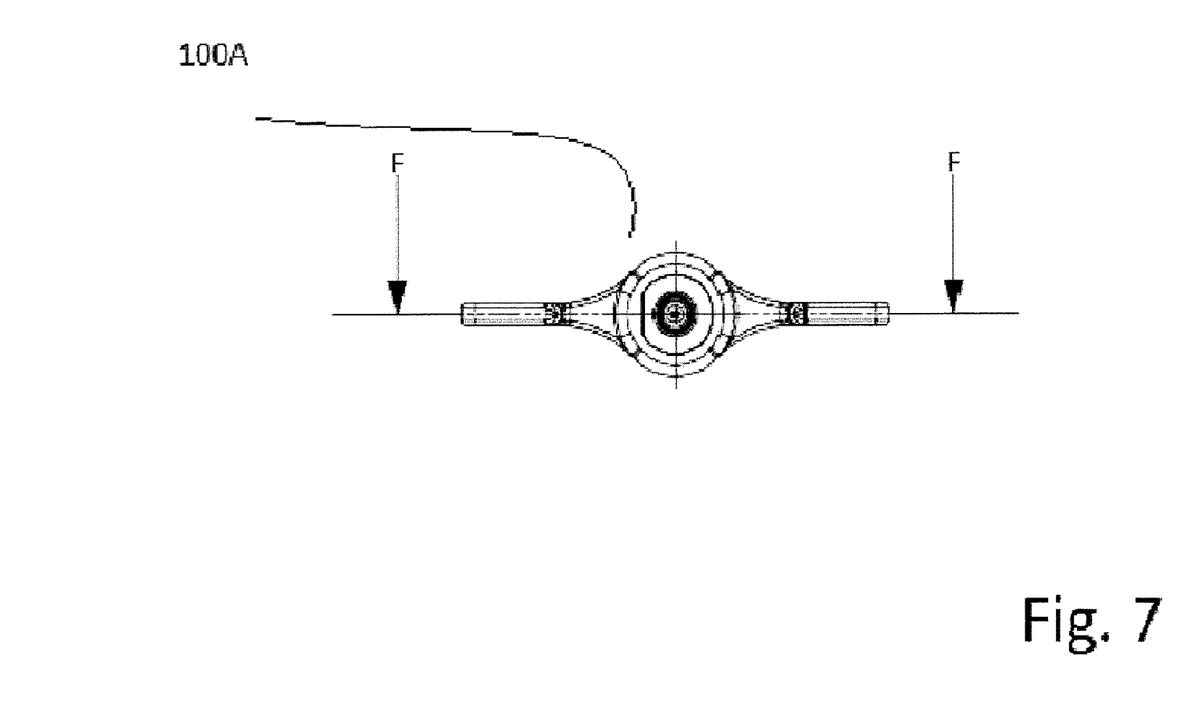
FIG. 7 is a bottom view of the another cranial fixation device in accordance with aspects of the disclosure.

FIG. 7 is a bottom view of the cranial fixation device 100A depicted in FIG. 6. As shown, the fixation device 100A including the opening 126 in which the cable 300 of the medical device can be inserted.

Figure 8:
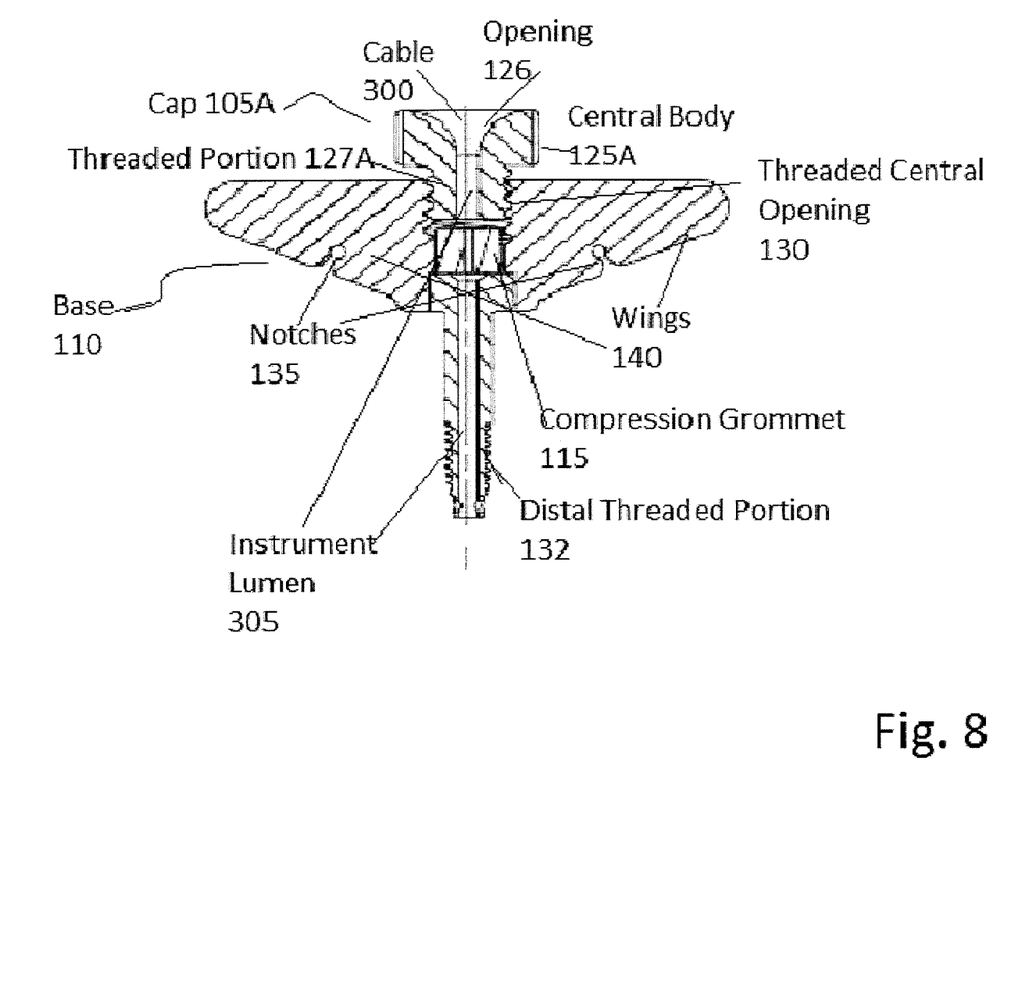
FIGS. 8-9 are sectional views of the another cranial fixation device along the F-F line of FIG. 7.
Figure 9:
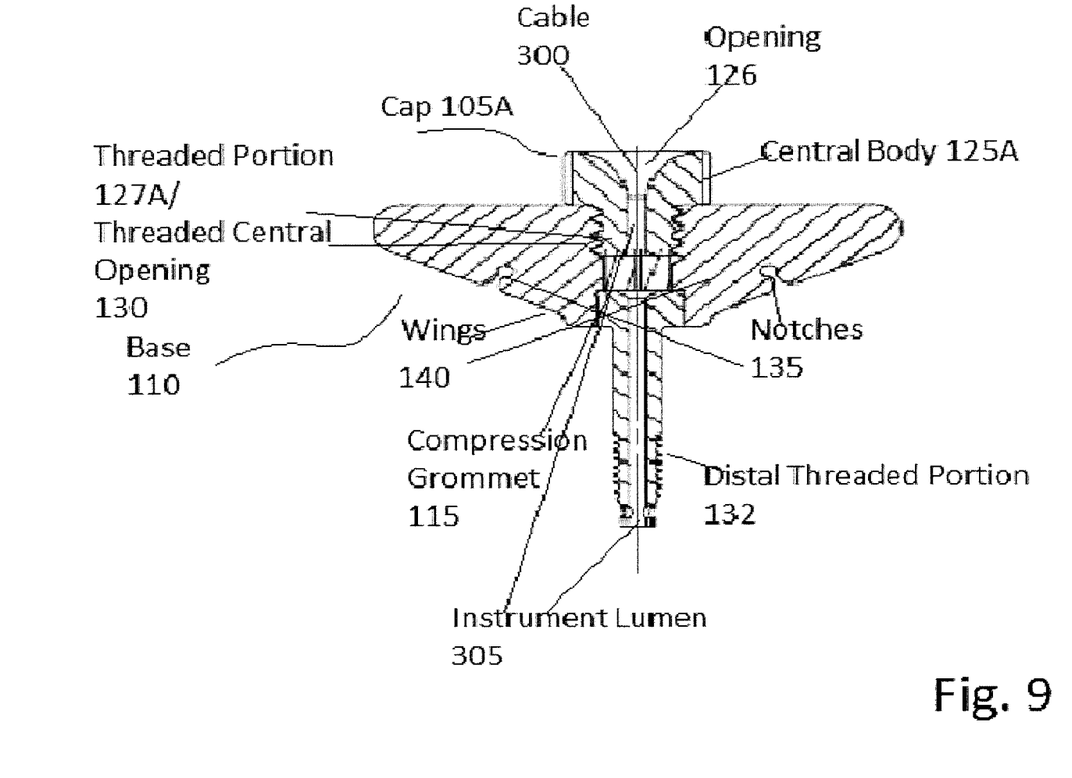

FIGS. 8-9 are sectional views of the cranial fixation device 100A along the F-F line of FIG. 7.

FIG. 8 depicts a sectional view of the cranial fixation device 100A in an opened state, e.g., not compressed. FIG. 9 depicts a sectional view of the cranial fixation device 100A in a closed state, e.g., compressed. In both figures, the medical device cable 300 is depicted as a dashed line traversing the instrument lumen 305. In the opened state, not compressed, the cap 105A is positioned to contact the compression grommet 115. The threaded portion 127A of the cap 105A is partially mated with the threaded central opening 130. In order to close the cranial fixation device 100A, the operator or user, twists or turns the central body 125A of the cap 105A to compress the compression grommet 115. Closing will occur once the medical device is positioned at a desired location within the skull. By twisting the central body 125A of the cap 105, the threaded portion 127A of the cap 105A further mates with the threaded central opening 130 of the base 110. The central body 125A of the cap 105A is twisted or turned until threaded portion 127A of the cap is fully mated with the threaded central opening 130 as shown in FIG. 9. Thus, as shown in FIG. 4, the cable 300 is secured in position where the threading acts as a torque stop.

The method for inserting a catheter or probe into the skull is similar to the method described above for the cranial fixation device 100. The base 110 of the cranial fixation device 100A is inserted in a preformed opening in the skull. In particular, the user will twist the base 110 such that the distal threaded portion 132 engages in the opening. At the time the base 110 is inserted into the preformed opening, the compression grommet 115 may already be positioned within the threaded central opening 130. Alternatively, the compression grommet 115 can be inserted into the threaded central opening of the base 100 after the base 110 is inserted into the preformed opening. The cap 105A is aligned with the compression grommet 115 and base 110 in an opened (uncompressed state). Subsequently, the cable 300 of the catheter or probe is inserted into the instrument lumen 305 and notches 135. Initially, the cable 300 is inserted in the opening 126 of the cap 105A and opening of the threaded portion 127A. The cable 300 is then advanced into the opening 116 of the compression grommet. The cable 300 is further advanced into the distal thread portion 132 which has an opening. The cable 300 is subsequently advanced until, the catheter or probe is at a desired depth. When the catheter or probe is at a desired depth, the cranial fixation device 100A is closed, as described above. For example, the central body 125A of the cap 105A is twisted by the user causing the threaded portion 127A of the cap 105A to further mate with the threaded central opening 130 of the base 110. The central body 125A of the cap 105 is twisted or turned until threaded portion 127A of the cap is fully mated with the threaded central opening 130 as shown in FIG. 9. Thus, as shown in FIG. 9, the cable 300 is secured in position where the threading acts as a torque stop.

Additionally, when the catheter or probe is at a desired depth, the cable 300 is inserted into the notches 135.

Alternatively, instead of inserting the cable 300 of the catheter or probe into the cap 105A, when the cap is aligned, the cable 300 of the catheter or probe can be inserted into the cap 105A prior to alignment.

The terminology used herein is for the purpose of describing particular embodiments only and is not intended to be limiting the scope of the disclosure and is not intended to be exhaustive. Many modifications and variations will be apparent to those of ordinary skill in the art without departing from the scope and spirit of the disclosure.

What is claimed is:

1. A cranial fixation device comprising:
    a cap comprising:
        a central body having a mating connector with a threaded portion projecting from a distal end of the central body;
        a pair of wings extending radially out from the central body; and
        a first opening extending from a proximal end of the central body to the distal end of the central body and through the threaded portion of the mating connector, a base comprising:
        a threaded central opening corresponding to the threaded portion of the mating connector, the threaded central opening being positioned on a proximal end of the base;
        a distal threaded portion configured to engage with an opening in a skull;
        a pair of wings extending radially out from the threaded central opening; and
        a second opening extending through the threaded central opening and the distal threaded portion; and
        a compression grommet configured to be placed into the threaded central opening of the base, the compression grommet having a third opening extending from a proximal end of the compression grommet to a distal end of the compression grommet, the first opening, the second opening and the third opening being aligned when the cap mates with the base and forms an instrument lumen configured to accept a portion of an instrument cable,
    the threaded portion of the cap being configured to mate with the threaded central opening of the base, and
    at least one wing of the pair of wings of the cap having a projection protruding in a direction towards the base, and each wing of the pair of wings of the base having a seat,
    wherein, when the instrument cable extends through the instrument lumen, the projection from at least one wing of the pair of wings of the cap and at least one of the seats in the pair of wings of the base are configured to create a torque stop when a predetermined compression of the compression grommet is applied by tightening the cap on the base, and
    when the predetermined compression of the compression grommet is applied, the compression grommet compresses against the instrument cable fixing the instrument cable in place at a determined depth.

2. The cranial fixation device of claim 1, wherein when the predetermined compression of the compression grommet is applied, the pair of wings of the cap are aligned with the pair of wings of the base.

3. The cranial fixation device of claim 1, wherein the threaded portion of the mating connector, the projection from at least one wing of the pair of wings of the cap and at least one of the seats in the pair of wings of the base are configured such that when the predetermined compression of the compression grommet is applied, a distal end of the threaded portion mates with the threaded central opening, the pair of wings of the cap are aligned with the pair of wings of the base and the projection from at least one of the pair of wings of the cap and at least one of the seats in the pair of wings of the base creates the torque stop.

4. The cranial fixation device of claim 1, wherein each wing of the pair of wings of the base further comprises a notch configured to receive a portion of the instrument cable.

5. The cranial fixation device of claim 4, wherein each notch is located on a distal portion of each wing, respectively.

6. The cranial fixation device of claim 5, wherein when a portion of the instrument cable is received in the respective notches, a portion of the instrument cable extends between the respective notches.

7. The cranial fixation device of claim 1, wherein each wing of the pair of wings of the cap comprises a projection towards the direction of the base, and each wing of pair of wings of the base comprises a corresponding seat, each projection and the corresponding seat forming a torque stop when the predetermined compression of the compression grommet is applied by tightening the cap on the base.

8. The cranial fixation device of claim 1, wherein the instrument lumen has a diameter dimensioned for slidably accepting the instrument cable.

9. The cranial fixation device of claim 1, wherein the determined depth is adjustable.

10. The cranial fixation device of claim 1, wherein the pair of wings of the cap extends symmetrically in opposite directions with respect to the central body and wherein the pair of wings of the base extend symmetrically in opposite directions with respect to the threaded central opening.

11. The cranial fixation device of claim 1, wherein the first opening has a larger diameter at the proximal end of the central body than the distal end of the central body.

12. The cranial fixation device of claim 1, wherein the threaded portion has a male threading.

13. The cranial fixation device of claim 1, the projection being located on a distal end of at least one wing of the pair of wings of the cap.

14. The cranial fixation device of claim 1, wherein the pair of wings of the cap are configured to facilitate mating the cap to the base.

15. A cranial fixation device comprising:
   a base comprising:
   a threaded central opening positioned on a proximal end of the base, the threaded central opening configured to mate with a mating connector of a cap;
   a distal threaded portion configured to engage with an opening in a skull;
   an opening extending through the threaded central opening and the distal threaded portion, the opening configured to receive a portion of an instrument cable; and
   a pair of wings extending radially out from the threaded central opening, each wing having a notch configured to receive another portion of the instrument cable;
   wherein each notch is located on a distal portion of each wing, respectively.

16. The cranial fixation device of claim 15, wherein when a portion of the instrument cable is received in the respective notches, a portion of the instrument cable extends between the respective notches.

17. The cranial fixation device of claim 16, wherein the threaded central opening is further configured to receive a compression grommet, each wing of the pair of wings has a seat, each seat configured to form a torque stop by engaging with a corresponding projection in a cap when a predetermined compression of the compression grommet is applied responsive to the cap mating with the base.

18. A cranial fixation device comprising:
   a cap comprising:
   a central body having a mating connector with a threaded portion projecting from a distal end of the central body;
   a first opening extending from a proximal end of the central body to the distal end of the central body and through the threaded portion of the mating connector, a base comprising:
   a threaded central opening corresponding to the threaded portion of the mating connector, the threaded central opening being positioned on a proximal end of the base;
   a distal threaded portion configured to engage with an opening in a skull;
   a pair of wings extending radially out from the threaded central opening; and
   a second opening extending through the threaded central opening and the distal threaded portion; and
   a compression grommet configured to be placed into the threaded central opening of the base, the compression grommet having a third opening extending from a proximal end of the compression grommet to a distal end of the compression grommet, the first opening, the second opening and the third opening being aligned when the cap mates with the base and forms an instrument lumen configured to accept a portion of an instrument cable,
   the threaded portion of the cap being configured to mate with the threaded central opening of the base,
   wherein, when the instrument cable extends through the instrument lumen, the dimensions of the threaded central opening and the threaded portion are configured to create a torque stop when a predetermined compression of the compression grommet is applied by tightening the cap on the base, and
   when the predetermined compression of the compression grommet is applied, the compression grommet compresses against the instrument cable fixing the instrument cable in place at a determined depth.

* * * * *